United States Patent [19]

Robinson

[11] Patent Number: 5,330,456
[45] Date of Patent: Jul. 19, 1994

[54] DISPOSABLE ABSORBENT PANEL ASSEMBLY

[75] Inventor: Robin K. Robinson, Tacoma, Wash.

[73] Assignee: Paragon Trade Brands, Inc., Federal Way, Wash.

[21] Appl. No.: 88,907

[22] Filed: Jul. 8, 1993

Related U.S. Application Data

[63] Continuation of Ser. No. 865,968, Apr. 9, 1992, abandoned.

[51] Int. Cl.$^5$ .................... A61F 13/50; A61F 13/46
[52] U.S. Cl. .................... 604/368; 604/378; 604/380; 604/358
[58] Field of Search ............ 604/378, 380, 368, 379

[56] References Cited

U.S. PATENT DOCUMENTS

| | | | |
|---|---|---|---|
| 3,545,441 | 12/1970 | Gravdahl | 604/380 |
| 3,888,257 | 6/1975 | Cook et al. | |
| 4,333,463 | 6/1982 | Holtman | |
| 4,336,803 | 6/1982 | Repke | |
| 4,364,992 | 12/1982 | Ito et al. | |
| 4,392,861 | 7/1983 | Butterworth et al. | |
| 4,685,915 | 8/1987 | Hasse et al. | 604/378 |
| 4,798,603 | 1/1989 | Meyer et al. | 604/378 |
| 4,834,735 | 5/1989 | Alemany et al. | 604/368 |
| 4,927,346 | 5/1990 | Kaiser et al. | |
| 4,988,344 | 1/1991 | Reising et al. | 604/368 |
| 5,017,324 | 5/1991 | Kaiser et al. | |
| 5,019,063 | 5/1991 | Marsan et al. | 604/368 |

FOREIGN PATENT DOCUMENTS 0716809  10/1954  United Kingdom ............ 604/378

Primary Examiner—Randall L. Green
Assistant Examiner—D. Willse
Attorney, Agent, or Firm—Dressler, Goldsmith, Shore & Milnamow, Ltd.

[57] ABSTRACT

A disposable absorbent panel assembly including a fibrous absorbent panel and a liquid transfer layer. The fibrous absorbent panel includes front and rear end panel portions, and central panel section extending between the end panel portions. The central panel section has opposite side edge panel portions and a central panel portion positioned between the side edge panel portions. The end panel portions have a relatively lesser basis weight than the side edge central portions. The fibrous absorbent panel contains highly-sorbent superabsorbent material which is substantially confined to the central panel portion. The liquid transfer layer is positioned above the fibrous absorbent panel and extends longitudinally thereof at least along the length of the central panel portion. The liquid transfer layer promotes wicking and distribution of liquid within the absorbent panel assembly.

9 Claims, 2 Drawing Sheets

DISPOSABLE ABSORBENT PANEL ASSEMBLY

This application is a continuation division of application Ser. No. 07/865,968, filed Apr. 9, 1992, now abandoned.

TECHNICAL FIELD

The present invention relates to a new and improved absorbent panel assembly suitable for use in disposable absorbent articles such as disposable diapers, disposable incontinent briefs, and the like. More particularly, the invention relates to such a panel assembly that includes a centrally zoned deposition area of superabsorbent material and a liquid transfer layer positioned above the deposition area.

BACKGROUND OF THE INVENTION

Disposable absorbent articles usually have an absorbent panel assembly containing superabsorbent material to increase the absorbent capacity of the panel assembly while reducing the bulkiness of the article.

In order for the superabsorbent material to function, the liquid being absorbed must be transported to the superabsorbent material. In other words, the superabsorbent material must be placed in a position to be contacted by liquid discharged onto the absorbent panel assembly. Furthermore, as the superabsorbent material absorbs liquid, it must be allowed to swell. If the superabsorbent material is prevented from swelling, it will cease to absorb liquid. Hence, if the superabsorbent material is to function in absorbent articles wherein the liquid to be absorbed is discharged in a small void area, the configuration of the panel assembly containing the superabsorbent material is of significant importance.

Particular absorbent panel constructions contain a zoned region of superabsorbent material in a selected portion of the panel in an attempt to make efficient use of the superabsorbent material.

U.S. Pat. No. 3,888,257, to Cook et al., shows an absorbent panel construction including a 3-dimensional dispersion of superabsorbent material along a central zone of an absorbent panel.

U.S. Pat. No. 4,333,463, to Holtman, discloses an absorbent pad which contains a zoned region of superabsorbent material in its front upper or lower portion.

U.S. Pat. No. 4,927,346, to Kaiser et al., discloses a method for forming an absorbent panel containing a layer of superabsorbent material in a predetermined portion of thickness of the absorbent panel. One embodiment illustrates the layer of superabsorbent material positioned above a lower portion of the panel which is substantially free of superabsorbent material.

U.S. Pat. No. 4,685,915, to Hasse et al., discloses an hourglass shaped absorbent pad having a central portion of relatively high absorbent capacity, with the embodiment of FIGS. 7 through 10 showing a pad construction wherein a central portion has a higher basis weight than front and rear end portions, and side end portions. Particulate superabsorbent polymer is deposited only in the central portion.

U.S. Pat. No. 4,798,603, to Meyer et al., shows an absorbent assembly including a liquid transport layer positioned atop an absorbent pad of the construction to improve liquid spread and distribution. In the embodiment of FIGS. 3 and 4, transport layer is illustrated as overlying a central portion of a hourglass shaped absorbent panel, between the leg cutouts thereof.

SUMMARY OF THE INVENTION

A disposable absorbent panel assembly embodying the principles of the present invention includes a fibrous absorbent panel and a liquid transfer layer. The fibrous absorbent panel includes front and rear end panel portions, and a central panel section extending between the end panel portions. The central panel section has opposite side edge panel portions and a central panel portion positioned between the side edge panel portions. The end panel portions have a relatively lesser basis weight than the side edge central portions. The fibrous absorbent panel comprises fiberized wood pulp and highly-sorbent superabsorbent material which is substantially confined to the central panel portion. The liquid transfer layer is positioned above the fibrous absorbent panel and extends longitudinally thereof at least along the length of the central panel portion. The liquid transfer layer promotes wicking and distribution of liquid within the absorbent panel assembly.

In the illustrated embodiments, the side edge panel portions have relatively greater density than the central panel portion. A leg cutout is defined along and in each densified side edge panel portion to promote the fit around a wearer's body.

In accordance with the incontinent brief embodiment, the absorbent panel assembly is interposed between a hydrophobic topsheet and a backsheet. The topsheet has a surfactant-treated central portion which is positioned above the liquid transfer layer.

Other features and advantages of the present invention will become readily apparent from the following detailed description, the accompanying drawings, and the appended claims.

DETAILED DESCRIPTION

Figure 1:
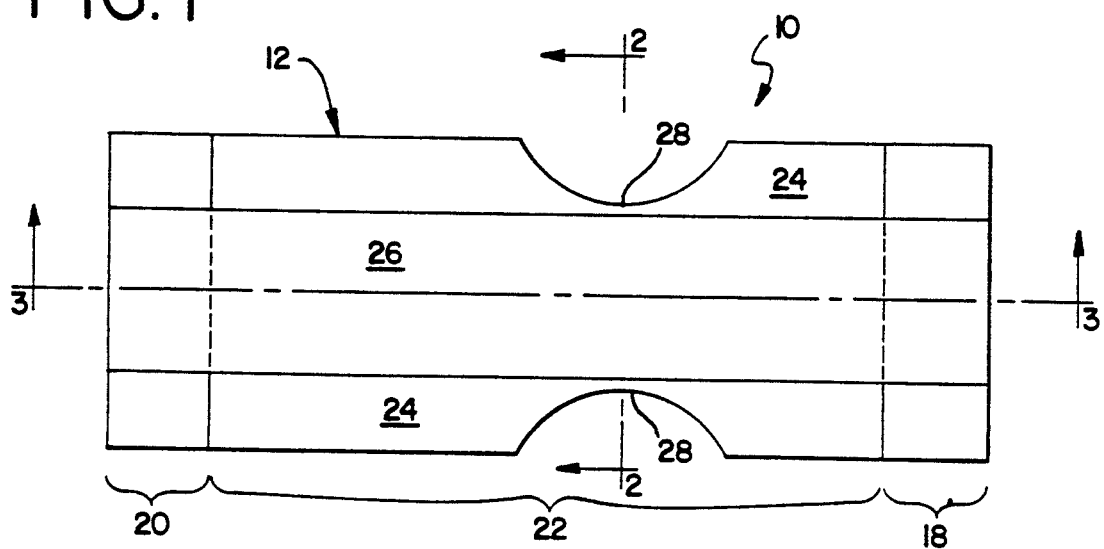
FIG. 1 is a plan view of an absorbent panel assembly embodying the principles of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

Referring now to the drawings, FIG. 1 shows one embodiment of an absorbent panel assembly in accordance with the present invention. The absorbent panel assembly 10 comprises a fibrous absorbent panel 12, a tissue layer 14 and a liquid transfer layer 16.

Figure 3:
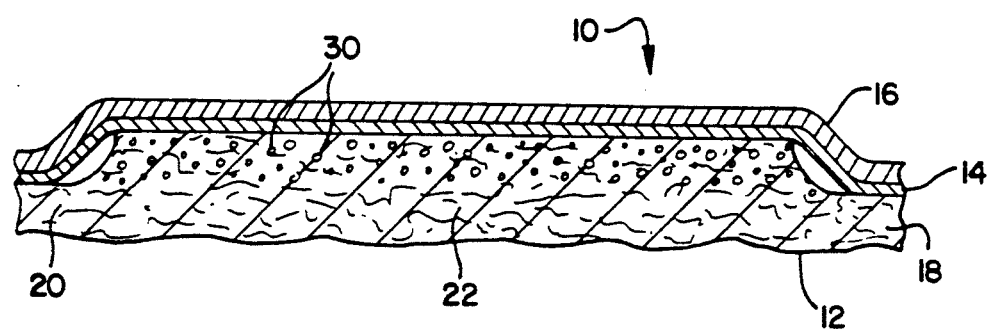
FIG. 3 is a cross-sectional view taken along lines 3—3 of FIG. 1.

The fibrous absorbent panel 12 is generally rectangular in shape and comprises an absorbent fibrous web initially formed with a substantially uniform basis weight. The fibrous absorbent panel 12 includes longitudinally spaced front end panel portion 18 and a rear end panel portion 20. As shown in FIG. 3, the front and rear end panel portions 18, 20 are scarfed to have a smaller web basis weight than a central panel section 22 extending therebetween, with a longitudinal density profile being substantially the same.

Figure 2:
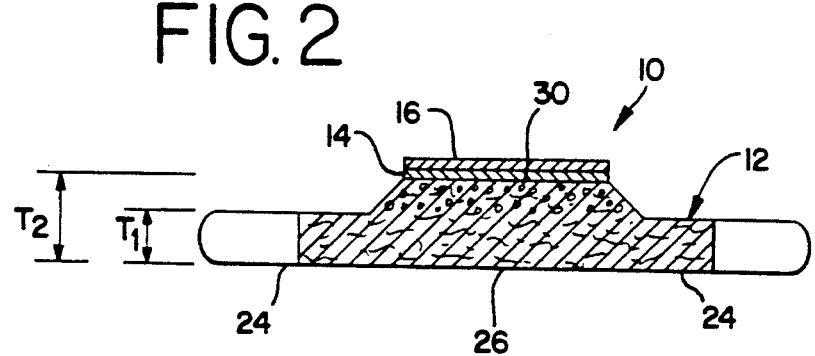
FIG. 2 is a cross-sectional view taken along lines 2—2 of FIG. 1.

The central panel section 22 comprises laterally spaced side edge panel portions 24 and a central panel portion 26 positioned between the side edge panel portions 24. As best seen in FIG. 2, the side edge panel portions 24 are densified by calendering to have relatively greater density and a smaller thickness $T_1$ than the density and thickness $T_2$ of the central panel portion 26, with the profile of the web basis weight, laterally of the web, being substantially constant.

There are disposed leg cutouts 28 along and in the densified side edge panel portions 24 (which densification promotes panel stability and integrity during formation of the cutouts) to promote a fit of a garment including the present absorbent panel assembly 10. The leg cutouts 28 are respectively arcuate and are positioned symmetrically with respect to a lateral centerline. Preferably, the leg cutouts 28 each defined a segment of a circle, and are disposed slightly forwardly to the front end panel portion 18 along the length of the fibrous absorbent panel 12.

The absorbent panel 12 contains highly-sorbent superabsorbent material 30 distributed therein. Preferably, such superabsorbent material 30 is substantially confined to the central panel portion 26. More preferably, about a top half portion of the central panel portion 26 contains the superabsorbent material 30, as shown in FIGS. 2 and 3, to form a zoned superabsorbent area which laterally extends to an approximate area of the leg cutouts 28.

The liquid transfer layer 16 is positioned above the absorbent panel 12 to overlie at least the zoned superabsorbent area thereof. The liquid transfer layer 16 preferably extends longitudinally about the full length of the absorbent panel 12, and laterally to a width less than the spacing between the leg cutouts 28. More preferably, the transfer layer 16 extends longitudinally about the length of the central panel portion 26, and laterally to a width corresponding to the zoned superabsorbent area.

The tissue layer 14 is substantially coextensive with the liquid transfer layer 16 and is positioned between the liquid transfer layer 16 and the central panel section 22 of the absorbent panel 12. The tissue layer 14 extends approximately the length of the absorbent panel 12 and the width of the zoned superabsorbent area.

The liquid transfer layer 16 serves to promote liquid wicking and distribution of liquid within the absorbent panel assembly 10. The tissue layer 14 is employed to help reduce migration of superabsorbent material outwardly through the transfer layer 16, but for some applications may be omitted.

Figure 4:
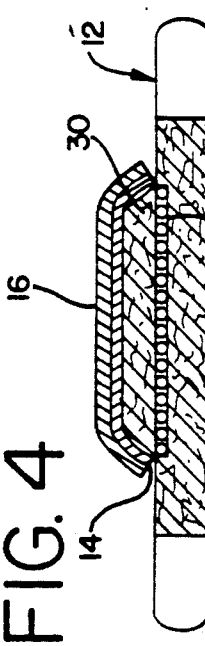
FIG. 4 is a cross-sectional view illustrating another embodiment of the absorbent panel assembly.

While illustrated as being homogeneously or uniformly mixed in at least a portion of the absorbent panel 12, the superabsorbent material may be placed in a layered form within the absorbent panel 12 to provide a superabsorbent layer 32 spaced from the upper surface of the absorbent panel 12, as shown in FIG. 4. The superabsorbent layer 32 is preferably positioned at or adjacent the thickness $T_1$ in the central panel portion 26 of the fibrous absorbent panel 12. It is more preferred that the superabsorbent layer 32 is substantially in a direct liquid-transferable relationship with the densified side panel portions 24. Likewise, the liquid transfer layer 16 and the tissue layer 14 respectively may preferably be laterally coextensive with the superabsorbent layer 32.

The absorbent fibrous web of the absorbent panel 12 is comprised of hydrophilic fibers, such as rayon fibers, cellulosic fibers, peat moss, acrylic fibers, synthetic pulp fibers, meltblown fibers, and the like. The cellulosic fibers include tissue, wood pulp fibers, cotton linters, and the like. The wood pulp fibers generally are those that are used to form the fluff or fibrous batt layer in conventional absorbent articles such as disposable diapers. Other cellulosic fibers that might be used are flax, hemp, jute, ramie, cotton and the like.

The liquid transfer layer 16 may comprise porous plastic foam, a bonded fibrous web, and the like. A suitable bonded web may include thermally-bonded, meltblown, or spunbonded nonwoven fabric. Such nonwoven fabric may preferably be made of resilient fibers such as polyethylene, polypropylene, polyester, nylon, bicomponent fibers, and the like. These fibers may be treated to be hydrophilic, if desired.

The superabsorbent material 30 is generally a water-insoluble but water-swellable polymeric substance capable of absorbing water in an amount which is at least 10 times the weight of the substance in its dry form. The superabsorbent material 30 is in the form of particles which may be in shape of fibers, spheres, bits of film, globules, or the like. Typical polymeric substances include carboxylated cellulose, polysaccharides, acrylic acid derivative polymers, polyacrylonitrile derivatives, polyacrylamide, polyvinyl alcohol, and the like.

Figure 5:
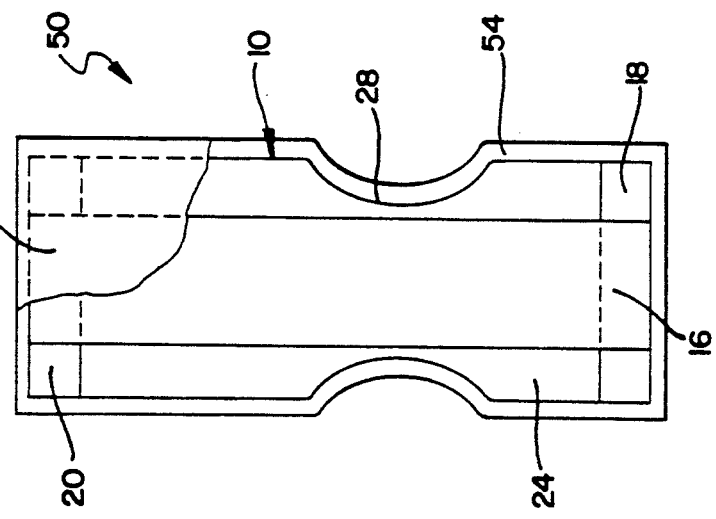
FIG. 5 is a plan view of a incontinent brief embodiment of the present invention wherein a major part of a topsheet is torn away to show the underlying absorbent panel assembly.

FIG. 5 shows an exemplary incontinent brief embodying the absorbent panel assembly of the present invention. The incontinent brief 50, includes a topsheet 52, a backsheet 54 and the present absorbent panel assembly 10 interposed therebetween. The topsheet 52 and the backsheet 54 are secured together at their peripheries to enclose the absorbent panel assembly 10 therein. The topsheet 52 is preferably of hydrophobic material which is surfactant-treated in its lateral center portion substantially overlying the liquid transfer layer 16 of the absorbent panel assembly 10.

The absorbent assembly 10 includes a fibrous absorbent panel 12. The absorbent panel 12 is generally rectangular and approximately 240 mm wide and 684 mm long, with small leg cutout 28 in opposite sides thereof.

The fibrous absorbent panel 12 comprises a fiberized fluff pulp having a basis weight of from about 200 to about 600 g/m$^2$, preferably of about 500 g/m$^2$, and a density of from about 0.05 to about 0.11 g/cc, preferably of 0.08 g/cc. The fluff pulp is scarfed in the cross-direction at the longitudinal front and rear end panel portions 18, 20 so that the both end panel portions have a basis weight of from about 100 to about 400 g/m$^2$, preferably of 200 g/m$^2$. The scarfed area at the both end panel portions may have different scarfing lengths but will typically be between 1 and 10 inches in length.

The central panel section 22 of the fluff pulp has opposite side edge panel portions 24 or leg cutout zones each about 2 inches wide, which edge panel portions are densified to have a higher density of from about 0.08 to about 0.13 g/cc, preferably of 0.12 g/cc. The leg cutout zone 24 runs between the front and rear end panel portions 18, 20. The leg cutout 28 is formed in each of the densified leg cutout zones 24. Each leg cutout 28 is located at approximately 170 - 200 mm from the front edge of the absorbent panel 12 and is approximately 170 mm long and approximately 45 mm deep. The radius of the cutout circle may be consistent.

The absorbent panel 12 further contains a zoned area of commercially available superabsorbent polymer 30 in the approximate area of the leg cutouts 28. The zoned area of the superabsorbent polymer 30 may be mixed homogeneously with the top one-half of the fluff layer in the central panel portion 26. Alternatively, a zoned layer of the superabsorbent polymer 30 may be placed intermediate upper and lower layers of fluff pulp, each having a basis weight of from about 100 to about 300 g/m$^2$.

The topsheet 52 is typically made of carded, spunlaced, spunbonded, or thermally-bonded polypropylene or polyester nonwoven fabric, as is well known in the art. The lateral central portion of the topsheet 52 is treated to hydrophilic with 0.1 to 1.0 wt. % of the surfactant.

The backsheet 54 typically comprises a liquid-impervious material, such as plastic film or sheet. Suitable materials include a polyethylene or polyethylene terephthalate sheet having a thickness of the order of 0.0005 to 0,001 inches. Nonwoven materials exhibiting liquid-impermeability can be used, as can composite or laminate sheet materials such as comprising integrated nonwoven fabric and polymeric film layers.

Figure 6:
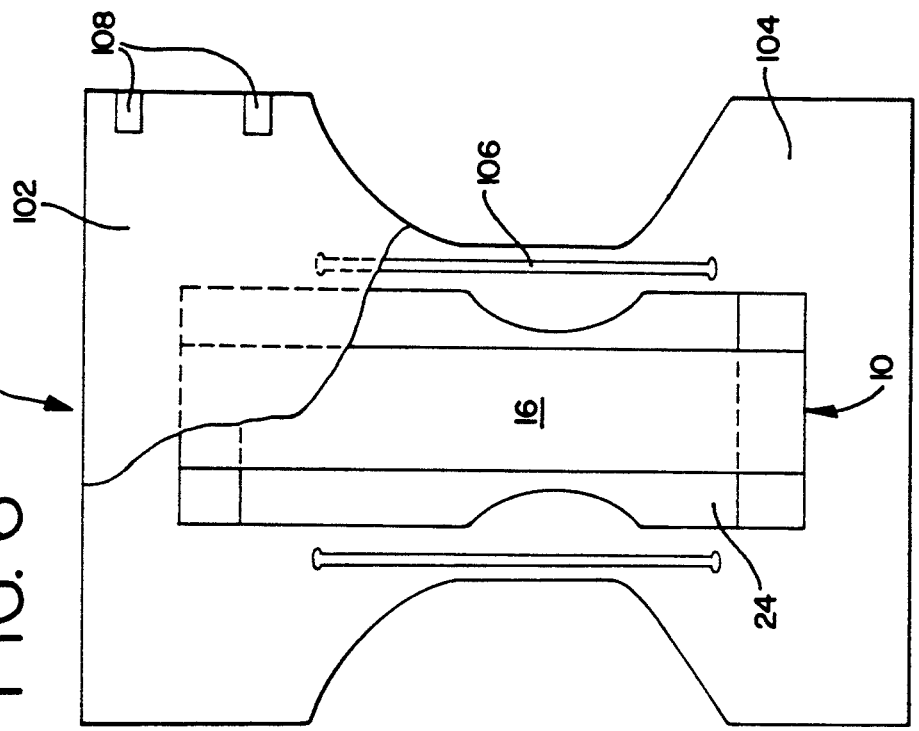
FIG. 6 is a plan view of a disposable diaper embodiment of the present invention wherein a major part of a topsheet is broken to show the underlying other diaper elements including the absorbent panel assembly.

FIG. 6 shows an exemplary integral disposable diaper embodying the absorbent panel assembly of the present invention. While the illustrated diaper embodiment is intended for incontinence use by adults, it is to be understood that disposable diapers may be appropriately sized for use by infants, or babies.

The disposable diaper 100 includes the absorbent panel assembly 10 in accordance with the present invention. The diaper 100 further includes a hydrophobic topsheet 102 which has a surfactant-treated lateral center portion substantially overlying the liquid transfer layer 16 of the panel assembly 10. The diaper 100 further includes a backsheet 104 positioned on the side of the absorbent panel assembly 10 which is opposite the topsheet 102. An elastic element 106 is stretchably disposed between the topsheet 102 and the backsheet 104, adjacent and along each leg cutout zone 24 of the absorbent panel assembly 10 to provide a leg elastic gather. Adhesive tape fasteners 108, only one pair of which are shown in FIG. 6, as well known in 10 the art, are provided on the rearward portions of the diaper 100. Each of these fasteners 108 includes a tab-like element having pressure-sensitive adhesive thereon which, when brought into contact with a landing area associated with the forward, outer waist portion of the diaper 100, secures the diaper 100 in position. The diaper 100 may also be provided with elasticized waistband, as is well known in the art.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. The disclosure is intended to cover by the appended claims all such modifications as fall within the scope of the claims.

What is claimed is:

1. A disposable absorbent panel assembly, comprising:

a fibrous absorbent panel comprising fiberized wood pulp, said panel including front and rear end portions, spaced apart side edge portions extending longitudinally between said end portions, and a central portion positioned between said side edge portions and extending longitudinally between said end portions, the fibrous material of said side edge portions having a relatively greater density than the fibrous material of said central portion;

said absorbent panel further comprising highly-sorbent superabsorbent material substantially confined to said central portion thereof to form a zoned superabsorbent area which extends laterally approximately to said relatively denser side edge portions, which said side edge portions are relatively free of superabsorbent material; and a liquid transfer layer comprising resilient material and positioned above said absorbent panel for overlying at least said central portion of the absorbent panel so that liquid can flow downwardly through said transfer layer into said absorbent panel, said transfer layer promoting wicking and distribution of liquid within said absorbent panel assembly.

2. An absorbent panel assembly in accordance with claim 1, wherein said side edge portions of said absorbent panel each define a leg cutout to promote fit of a garment including said panel assembly, said transfer layer having a width less than the spacing between leg cutouts.

3. An absorbent panel assembly in accordance with claim 2, wherein said side edge panel portions, and said central panel portion, including said superabsorbent material, are of generally equal densities.

4. An absorbent panel assembly in accordance with claim 2, wherein said side edge panel portions are of a relatively greater density than said central panel portion, including the superabsorbent material therein.

5. An absorbent panel assembly in accordance with claim 2, wherein said superabsorbent material is blended with the wood pump forming approximately the upper half of said central panel portion.

6. An absorbent panel assembly in accordance with claim 2, wherein said superabsorbent material is provided in a layer spaced from an upper surface of said absorbent panel, said central panel portion including a layer of wood pulp which is substantially free of superabsorbent material having a basis weight of about 100–300 g/m$^2$ positioned above said superabsorbent material.

7. A disposable absorbent article comprising:

a hydrophobic topsheet having a hydrophilic lateral center portion;

a liquid impermeable backsheet; and an absorbent panel assembly interposed between said topsheet and backsheet, said absorbent panel assembly comprising a fibrous absorbent panel comprising fiberized wood pulp, said panel including front and rear end panel portions, spaced apart side edge panel portions extending longitudinally between said end panel portions, and a central panel portion positioned between said side edge panel portions and extending longitudinally between said end panel portions, the fiberized wood pulp of said side edge panel portions having a relatively greater density than the fiberized wood pulp of said central panel portion, said absorbent panel further comprising high-sorbent superabsorbent material substantially confined to said central panel portion thereof to form a zoned superabsorbent area which extends laterally approximately to said relatively denser side edge portions, which said side edge portions are relatively free of superabsorbent material, and a liquid transfer layer comprising resilient material positioned between said hydrophilic center portion of the topsheet and said central panel portion of the absorbent panel, and overlying at least said central panel portion said liquid transfer layer promoting wicking and distribution of liquid from said hydrophilic center portion of the topsheet into said central panel portion of the absorbent panel.

8. A disposable absorbent article in accordance with claim 7, wherein said side edge panel portions of the absorbent panel have a density of from about 0.08 to about 0.13 g/cc.

9. A disposable absorbent article in accordance with claim 7, wherein said resilient material includes thermally-bonded, meltblown, or spunbonded nonwoven fabric.

* * * * *